US011559261B2

(12) United States Patent
Matsumura et al.

(10) Patent No.: US 11,559,261 B2
(45) Date of Patent: Jan. 24, 2023

(54) GAIT MOTION DISPLAY SYSTEM AND PROGRAM

(71) Applicant: Panasonic Intellectual Property Management Co., Ltd., Osaka (JP)

(72) Inventors: Yoshihiro Matsumura, Osaka (JP); Tomoharu Nakahara, Hyogo (JP); Tomohiko Fujita, Kyoto (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 431 days.

(21) Appl. No.: 15/776,391

(22) PCT Filed: Nov. 9, 2016

(86) PCT No.: PCT/JP2016/004835
§ 371 (c)(1),
(2) Date: May 15, 2018

(87) PCT Pub. No.: WO2017/085914
PCT Pub. Date: May 26, 2017

(65) Prior Publication Data
US 2018/0325467 A1    Nov. 15, 2018

(30) Foreign Application Priority Data
Nov. 19, 2015    (JP) .............................. JP2015-227096

(51) Int. Cl.
*A61B 5/00* (2006.01)
*G01C 22/00* (2006.01)
*A61B 5/11* (2006.01)

(52) U.S. Cl.
CPC ............ *A61B 5/743* (2013.01); *A61B 5/0077* (2013.01); *A61B 5/112* (2013.01); *A61B 5/1128* (2013.01);
(Continued)

(58) Field of Classification Search
CPC .................. A61B 5/1127; A61B 5/112; A61B 2562/0219; A61B 5/1128; A61B 5/743; G01C 22/006
(Continued)

(56) References Cited

U.S. PATENT DOCUMENTS 6,571,193 B1 *    5/2003  Unuma .................. G06V 40/23
                                                    340/853.2
7,292,151 B2 *  11/2007  Ferguson ............. A61B 5/1124
                                                    340/407.1
(Continued)

FOREIGN PATENT DOCUMENTS

CN          101327125 A      12/2008
EP          2005887 A1       12/2008
(Continued)

OTHER PUBLICATIONS

International Search Report and Written Opinion for corresponding App. No. PCT/JP2016/004835, dated Jan. 24, 2017.
(Continued)

*Primary Examiner* — Daniel L Cerioni
*Assistant Examiner* — Jonathan E. Cooper
(74) *Attorney, Agent, or Firm* — Renner, Otto, Boisselle & Sklar, LLP

(57) ABSTRACT

A gait motion display system including: a triaxial accelerometer, attached to the subject, that measures acceleration data of a subject in walking; an imaging unit that takes images of the subject in walking to obtain moving image data showing gait motions of the subject; a recording unit that records the acceleration data and the moving image data in synchronization with each other; an identification unit that converts the acceleration data recorded by the recording unit into horizontal displacement data and vertical displacement data, and identifies, from the moving image data, a repre-
(Continued)

sentative image corresponding to a representative motion in a gait cycle, based on the horizontal displacement data or the vertical displacement data; and a display that displays an image illustration of the representative motion in the gait cycle, with the representative image identified by the identification unit.

6 Claims, 7 Drawing Sheets

(52) U.S. Cl.
CPC .... *G01C 22/006* (2013.01); *A61B 2562/0219* (2013.01); *A61B 2576/00* (2013.01)

(58) Field of Classification Search
USPC ........................................................ 600/595
See application file for complete search history.

(56) References Cited

U.S. PATENT DOCUMENTS

| | | | | |
|---|---|---|---|---|
| 7,467,603 | B2* | 12/2008 | Davies | A01K 11/008 |
| | | | | 119/712 |
| 7,806,589 | B2* | 10/2010 | Tashman | A61B 6/505 |
| | | | | 378/197 |
| 8,007,450 | B2* | 8/2011 | Williams | A61B 5/1123 |
| | | | | 600/595 |
| 8,314,840 | B1* | 11/2012 | Funk | A61B 5/11 |
| | | | | 348/157 |
| 9,619,698 | B1* | 4/2017 | Chuang | A63B 24/0003 |
| 2006/0195050 | A1* | 8/2006 | Alwan | G06K 9/00335 |
| | | | | 600/595 |
| 2008/0086533 | A1* | 4/2008 | Neuhauser | A61B 5/4833 |
| | | | | 709/206 |
| 2009/0209830 | A1* | 8/2009 | Nagle | A43B 7/147 |
| | | | | 600/301 |
| 2011/0282828 | A1* | 11/2011 | Precup | G06K 9/00348 |
| | | | | 706/54 |
| 2012/0024061 | A1* | 2/2012 | Chiang | A61B 5/681 |
| | | | | 73/510 |
| 2012/0059432 | A1* | 3/2012 | Emborg | A61N 1/36003 |
| | | | | 607/49 |
| 2012/0136573 | A1* | 5/2012 | Janardhanan | G01C 21/20 |
| | | | | 701/512 |
| 2013/0142384 | A1* | 6/2013 | Ofek | H04W 4/023 |
| | | | | 382/103 |
| 2013/0324368 | A1* | 12/2013 | Aragones | G16H 20/30 |
| | | | | 482/8 |
| 2013/0325887 | A1* | 12/2013 | Takaoka | G06F 16/27 |
| | | | | 707/758 |
| 2015/0100251 | A1* | 4/2015 | Solinsky | G01L 19/0092 |
| | | | | 702/33 |
| 2015/0324636 | A1* | 11/2015 | Bentley | A63F 13/00 |
| | | | | 386/227 |
| 2016/0045140 | A1* | 2/2016 | Kitamura | A61B 5/1128 |
| | | | | 600/595 |
| 2016/0100790 | A1* | 4/2016 | Cantu | A61B 5/445 |
| | | | | 600/437 |
| 2016/0249829 | A1* | 9/2016 | Trabia | A43B 3/0015 |
| | | | | 600/592 |
| 2016/0314818 | A1* | 10/2016 | Kirk | G06F 1/163 |
| 2017/0027803 | A1* | 2/2017 | Agrawal | A61B 5/224 |

FOREIGN PATENT DOCUMENTS

| | | |
|---|---|---|
| JP | 2002-306628 | 10/2002 |
| JP | 2004-344418 | 12/2004 |
| JP | 2012-24275 | 2/2012 |
| JP | 2014-33739 | 2/2014 |

OTHER PUBLICATIONS

Chinese Office Action for Corresponding Application No. 201680066786.4 dated Apr. 15, 2021, along with English translation of search report.

* cited by examiner

GAIT MOTION DISPLAY SYSTEM AND PROGRAM

TECHNICAL FIELD

The present invention relates to a gait motion display system and program for displaying an image that shows a gait motion of a subject.

BACKGROUND ART

Gait motions of a subject are conventionally shown to the subject, in the fields of nursing care and rehabilitation, to provide coaching for proper gait motions. In a typical method, for example, an observer who is watching the moving image of the subject's gait motions extracts a predetermined image to display it.

Patent Literature (PTL) 1 discloses a three-dimensional motion analyzing device that determines the coordinate positions of each marker from moving image data obtained by taking images of a subject wearing a plurality of markers by a plurality of cameras, and analyzes the gait motions on the basis of the determined coordinate positions. The three-dimensional motion analyzing device disclosed in PTL 1 displays posture diagrams on the basis of the result of the analysis.

CITATION LIST

Patent Literature

PTL 1: Japanese Unexamined Patent Application Publication No. 2004-344418

SUMMARY OF THE INVENTION

Technical Problems

However, the above-described conventional method, which requires the observer to extract an image, has a problem in that a great burden is placed on the observer. Furthermore, since the selection of an image to be extracted is up to the experience and skills of the observer, the subject cannot receive coaching in the absence of a competent observer, which is inconvenient. Meanwhile, the three-dimensional motion analyzing device disclosed in PTL 1 requires the subject to wear a plurality of markers to take images by a plurality of cameras, and thus involves a complicated device structure.

In view of the above, the present invention aims to provide a highly convenient gait motion display system and program with a simple structure.

Solutions to Problems

To achieve the above object, the gait motion display system according to one aspect of the present invention includes: a triaxial accelerometer that measures acceleration data of a subject in walking, the triaxial accelerometer being attached to the subject; an imaging unit that takes images of the subject in walking to obtain moving image data showing gait motions of the subject; a recording unit that records the acceleration data and the moving image data in synchronization with each other; an identification unit that converts the acceleration data recorded by the recording unit into horizontal displacement data and vertical displacement data, and identifies, from the moving image data, a representative image corresponding to a representative motion in a gait cycle, based on the horizontal displacement data or the vertical displacement data; and a display that displays an image illustration of the representative motion in the gait cycle, together with the representative image identified by the identification unit.

Another aspect of the present invention is achieved in the form of a program that causes a computer to function as the above-described gait motion display system, or in the form of a computer-readable recording medium storing such program.

Advantageous Effect of Invention

The present invention is capable of providing a highly convenient gait motion display system with a simple structure.

DESCRIPTION OF EXEMPLARY EMBODIMENT

The following describes in detail the gait motion display system according to the embodiment of the present invention with reference to the drawings.

Note that the following embodiment shows an exemplary illustration of the present invention. The numerical values, shapes, materials, structural components, the arrangement and connection of the structural components, steps, the processing order of the steps etc. shown in the following embodiment are mere examples, and thus are not intended to limit the present invention. Of the structural components described in the following embodiment, structural components not recited in any one of the independent claims that indicate the broadest concepts of the present invention will be described as optional structural components.

Also note that the drawings are schematic diagrams, and thus they are not necessarily precise illustrations. Also, the same structural components are assigned with the same reference marks throughout the drawings.

Embodiment

Gait Motion Display System

First, an overview of the gait motion display system according to the present embodiment will be described with reference to FIG. 1 and FIG. 2.

Figure 1:
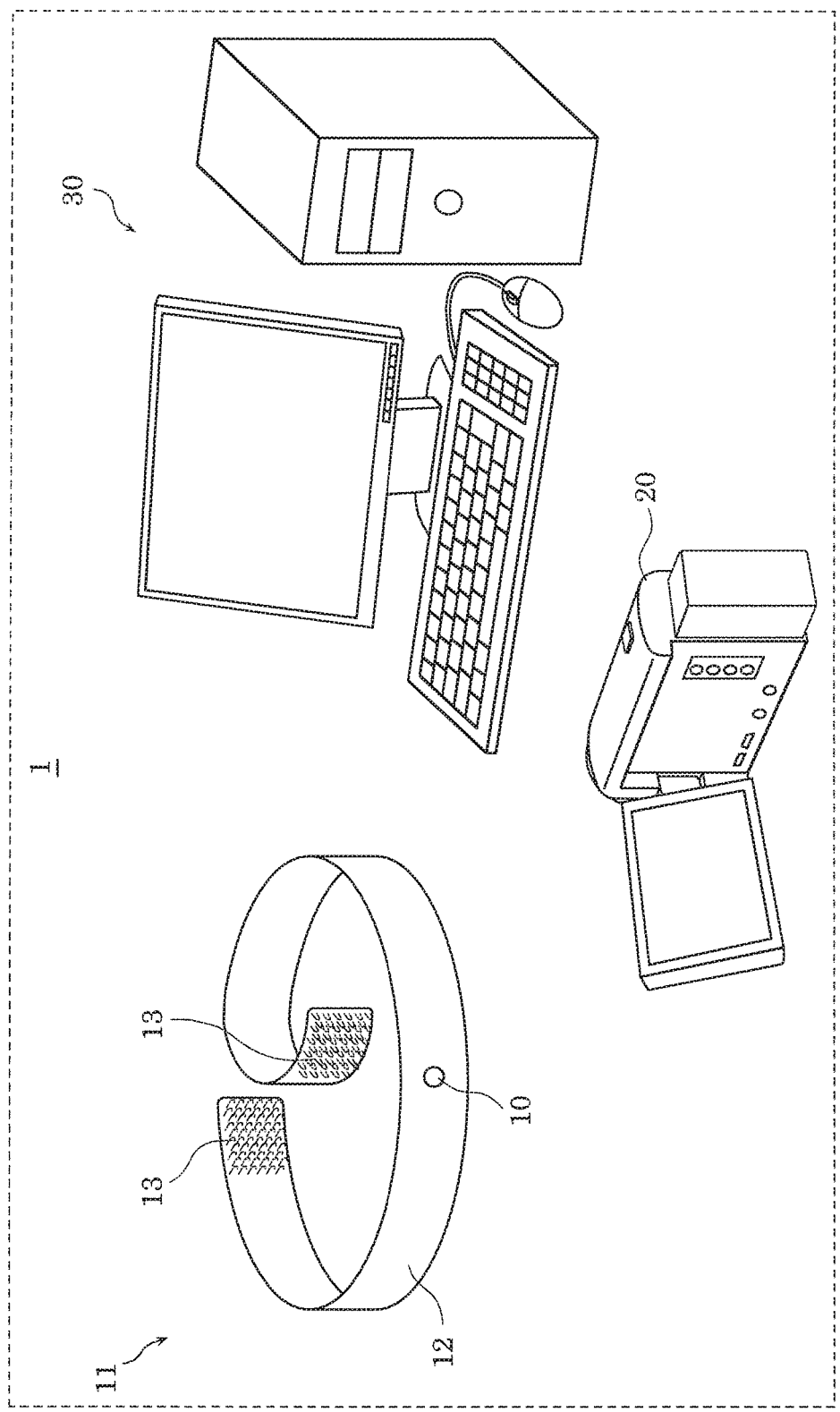
FIG. 1 is a diagram showing the structure of a gait motion display system according to an embodiment.
Figure 2:
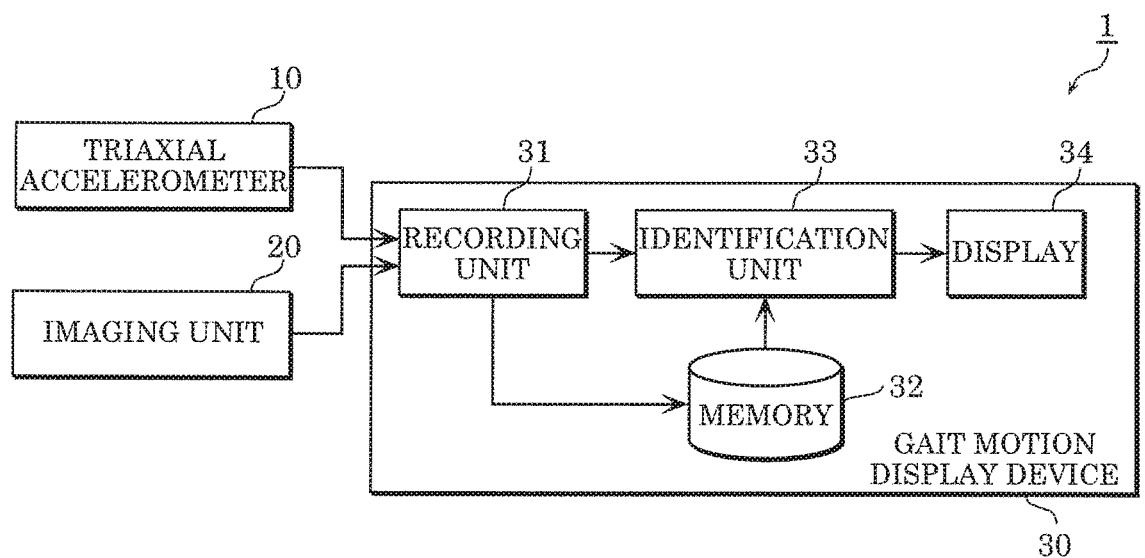
FIG. 2 is a block diagram showing the functional structure of the gait motion display system according to the embodiment.

FIG. 1 is a diagram showing a concrete structure of gait motion display system 1 according to the present embodiment. FIG. 2 is a block diagram showing a functional structure of gait motion display system 1 according to the present embodiment.

As shown in FIG. 1, gait motion display system 1 includes triaxial accelerometer 10, imaging unit 20, and gait motion display device 30. As shown in FIG. 2, gait motion display device 30 includes recording unit 31, memory 32, identification unit 33, and display 34.

The following describes in detail the structural components of the gait motion display system with reference to the drawings.

Triaxial Accelerometer

Figure 3:
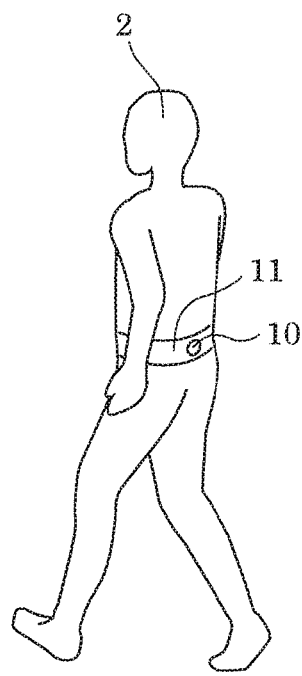
FIG. 3 is a diagram showing a triaxial accelerometer being attached to a subject in the gait motion display system according to the embodiment.

FIG. 3 is a diagram showing triaxial accelerometer 10 according to the present embodiment being attached to subject 2.

Triaxial accelerometer 10 is attached to subject 2 to measure acceleration data of subject 2 in walking. More specifically, triaxial accelerometer 10 measures, at a predetermined measurement rate, the acceleration of a body part of subject 2 at which triaxial accelerometer 10 is attached. Measurement rate is the number of times acceleration is measured per unit of time. Triaxial accelerometer 10 transmits the measured acceleration data to recording unit 31 of gait motion display device 30.

In the present embodiment, triaxial accelerometer 10 communicates with gait motion display device 30. Triaxial accelerometer 10 transmits the acceleration data to gait motion display device 30 by, for example, wireless communication. Wireless communication is performed in conformity with a predetermined wireless communication standard such as, for example, Bluetooth (registered trademark), Wi-Fi (registered trademark), and ZigBee (registered trademark).

The acceleration data measured by triaxial accelerometer 10 is three-dimensional acceleration vector data, which is, for example, data on the accelerations in the front-back direction, right-left direction, and up-down direction of subject 2. The acceleration data includes a plurality of measurement points. Each of the measurement points is associated with time information indicating the time at which such measurement point has been measured. Note that not all the measurement points are required to be associated with time information. For example, it is possible to calculate the time at which a measurement point not associated with time information has been measured, on the basis of the time information of a reference measurement point among a plurality of measurement points (e.g., the first measurement point) and on the basis of the measurement rate of the acceleration data.

In the present embodiment, as shown in FIG. 3, triaxial accelerometer 10 is attached at the lower back waist of subject 2. As shown in FIG. 1, triaxial accelerometer 10 is fixed to attachment 11. Worn by subject 2, attachment 11 enables triaxial accelerometer 10 to be attached at a predetermined body part of subject 2.

An example of attachment 11 is a belt that is worn around the waist of subject 2. As shown in FIG. 1, attachment 11 includes strap 12, and hook and loop fastener 13. The length of strap 12 is adjustable by putting together the hook surface and the loop surface of hook and loop fastener 13 at an appropriate position. More specifically, attachment 11 is worn around the waist of subject 2 by looping strap 12 around the waist of subject 2, and then by appropriately adjusting the length of strap 12 to tighten strap 12. Note that the means for adjusting the length of strap 12 is not limited to hook and loop fastener 13, and thus a buckle or another attachment may be employed.

As shown in FIG. 3, triaxial accelerometer 10 is attached at the waist of subject 2 by attachment 11 being worn around the waist of subject 2. Note that a body part of subject 2 at which triaxial accelerometer 10 is attached is not limited to the lower back waist, and thus may be the front side of the waist, or may be the head, the chest, a leg, an arm, etc.

Also note that attachment 11 is not limited to a belt, and thus may be clothes worn by subject 2. For example, triaxial accelerometer 10 may be fixed at the clothes, or may be held in a pocket of the clothes. Triaxial accelerometer 10 may include a fixture such as a hook and loop fastener, a safety pin, and a clip, and may be attached to the clothes by such fixture. Alternatively, triaxial accelerometer 10 may be directly attached on the skin of subject 2 by, for example, an adhesive sealing material.

Imaging Unit

Imaging unit 20 takes images of subject 2 in walking to obtain moving image data showing the gait motions of subject 2. Imaging unit 20 transmits the obtained moving image data to recording unit 31 of gait motion display device 30.

An unlimited example of imaging unit 20 is a video camera as shown in FIG. 1. Imaging unit 20 may also be a mobile terminal such as a smart phone, or may be a compact camera mounted on a personal computer (PC).

In the present embodiment, imaging unit 20 communicates with gait motion display device 30. Imaging unit 20 transmits the moving image data to gait motion display device 30 by, for example, wireless communication. Wireless communication is performed in conformity with a predetermined wireless communication standard such as, for example, Bluetooth (registered trademark), Wi-Fi (registered trademark), and ZigBee (registered trademark). Note that imaging unit 20 may be connected to gait motion display device 30 via a communication cable to perform wired communication.

The moving image data obtained by imaging unit 20 includes a plurality of images (frames). Each of the images is associated with time information indicating the time at which such image has been obtained. Note that not all the images are required to be associated with time information. For example, it is possible to calculate the time at which an image not associated with time information has been obtained, on the basis of the time information of a reference image among a plurality of images (e.g., the first frame) and on the basis of the frame rate of the moving image data.

Gait Motion Display Device

Gait motion display device 30 analyzes the gait motions of subject 2 on the basis of the acceleration data and the moving image data, and displays the result of the analysis. More specifically, gait motion display device 30 displays, as the result of the analysis, image illustrations of the representative motions in the gait cycle, together with the obtained images of subject 2.

Gait motion display device 30 is embodied, for example, as a computer and a monitor as shown in FIG. 1. More specifically, gait motion display device 30 includes: a non-volatile memory that stores a program; a volatile memory, which is a temporary storage region for the execution of the program: an input/output port; and a processor that executes the program. The functions of recording unit 31, memory 32, identification unit 33, display 34, and others are executed by the processor and the memories working in concert with one another.

Recording Unit

Recording unit 31 records the acceleration data measured by triaxial accelerometer 10 and the moving image data obtained by imaging unit 20 in synchronization with each other. More specifically, recording unit 31 associates the measurement points with the images on the basis of the time information of a plurality of measurement points in the acceleration data and the time information of a plurality of images in the moving image data, and stores the associated measurement points and images into memory 32.

For example, recording unit 31 associates one measurement point with an image with which time information is associated indicating the time closest to the time indicated by the time information of such measurement point. This is carried out for each of the measurements points. Consequently, the measurement points included in the acceleration data are associated with the images taken at approximately the same times as the times at which such measurement points have been measured. Note that when the measurement rate of the acceleration data and the frame rate of the moving image data are the same, recording unit 31 associates one measurement point with one image such that each of the remaining measurement points and images can be associated with each other in order of obtainment.

Note that when at least one of the acceleration data and the moving image data includes no time information, recording unit 31 may record the acceleration data and the moving image data in synchronization with each other, by use of the time at which recording unit 31 has received the acceleration data from triaxial accelerometer 10, or by use of the time at which recording unit 31 has received the moving image data from imaging unit 20. Recording unit 31 may use any method to synchronize the acceleration data and the moving image data.

Memory

Memory 32 is a memory that stores the acceleration data and the moving image data. The acceleration data and the moving image data recorded in memory 32 are synchronized with each other. More specially, the respective measurement points included in the acceleration data and the respective images taken at approximately the same times at which the measurement points have been measured are recorded in memory 32 in association with each other.

Identification Unit

Identification unit 33 converts the acceleration data recorded by recording unit 31 into horizontal displacement data and vertical displacement data. More specifically, identification unit 33 generates displacement data by second order integration of the acceleration data.

In the present embodiment, the acceleration data recorded by recording unit 31 is three-dimensional acceleration vector data measured by triaxial accelerometer 10. As such, identification unit 33 first converts three-dimensional acceleration vector data into three-dimensional displacement data, for example, and then separates the three-dimensional displacement data into horizontal and vertical displacement data. Note that identification unit 33 may first separate the three-dimensional acceleration vector data into horizontal acceleration data and vertical acceleration data, and then convert the respective data items into displacement data items.

Note that lower half frequency components of the gait frequency of the acceleration data in triaxial accelerometer 10 are affected by gravitational acceleration. For this reason, identification unit 33 applies the Fast Fourier Transform (FFT) to remove the low-frequency components from the acceleration data. Note that gait frequency is the reciprocal of the period (cycle) during which subject 2 takes two steps (one step for each foot). Identification unit 33 also removes, from the acceleration data, the acceleration components produced by the travelling of subject 2 to generate displacement data indicating only the amount of displacement produced by the gait motions of subject 2.

Identification unit 33 identifies, from the moving image data, a representative image corresponding to each of the representative motions in the gait cycle, on the basis of the horizontal displacement data or the vertical displacement data. More specifically, identification unit 33 extracts a characteristic point corresponding to each representative motion in the gait cycle from the horizontal displacement data or the vertical displacement data, and identifies, as the representative image, an image corresponding to the time of the extracted characteristic point. Note that the representative motions in the gait cycle will be described later with reference to FIG. 4.

The characteristic point is, for example, a local maximum value, a local minimum value, or a zero-crossing point in the horizontal displacement data, or the characteristic point is, for example, a local maximum value, a local minimum value, or a zero-crossing point in the vertical displacement data. The relationship between the characteristic point and each representative motion will be described later with reference to FIG. 5.

In the present embodiment, identification unit 33 further calculates walking time and the number of steps per predetermined unit of time, on the basis of the horizontal displacement data or the vertical displacement data. The walking time is a period during which subject 2 is in gait motions. The number of steps per predetermined unit of time is, for example, the number of steps per minute, which is calculated on the basis of the number of steps taken by subject 2 during the walking time.

Identification unit 33 further calculates a ratio between the right and left stance phases, on the basis of the horizontal displacement data or the vertical displacement data. The ratio between the right and left stance phases is a proportion between the duration of the stance phases of the left leg and the duration of the stance phases of the right leg. Such ratio is represented, for example, as each ratio of the stance phases of the left leg and each ratio of the stance phases of the right leg that take up the total duration of the both stance phases. The ratio between the right and left stance phases corresponds the right and left balance of the gait motions of subject 2.

Display

Display 34 displays the image illustration of each of the representative motions in the gait cycle, together with its representative image identified by identification unit 33. More specifically, display 34 displays a reporting screen that includes the image illustrations and their representative images.

Display 34 further displays the walking time and the number of steps calculated by identification unit 33. Display 34 further displays the ratio between the right and left stance phases calculated by identification unit 33. An example of the reporting screen displayed by display 34 will be described later with reference to FIG. 6.

Representative Motions in Gait Cycle

Figure 4:
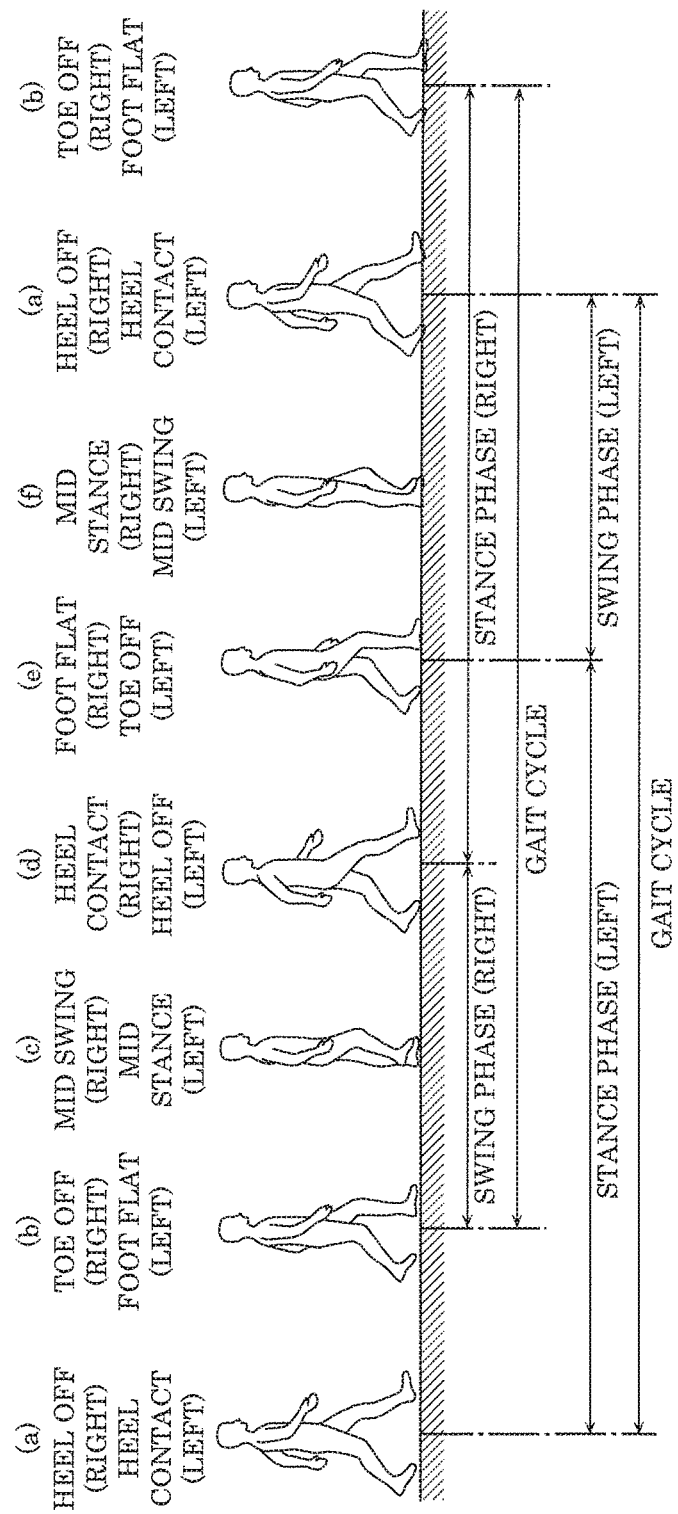
FIG. 4 is a diagram showing image illustrations of representative motions in a gait cycle.

The following describes the representative motions in the gait cycle with reference to FIG. 4. FIG. 4 is a diagram showing image illustrations of the representative motions in the gait cycle.

The gait cycle is a repetition period that starts with one motion and ends with the same motion in walking. For example, as shown in FIG. 4, a single period of the gait cycle starts from when the left foot heel contacts the ground to when the left foot heel contacts the ground again.

As shown in FIG. 4, the gait cycle includes stance phases and swing phases. The stance phase of the left leg is a period from when the left foot heel contacts the ground to when the left foot toe leaves the ground. The swing phase of the left leg is a period from when the left foot toe leaves the ground to when the left foot heel contacts the ground. The same is true of the right leg. Usually, the stance phase of the left leg includes the swing phase of the right leg, and the stance phase of the right leg includes the swing phase of the left leg.

The representative motions in the gait cycle include at least one of heel contact, foot flat, mid stance, heel off, toe off, and mid swing. As shown in FIG. 4, these motions are carried out by each of the left foot and the right foot. The following focuses on the left foot to describe the representative motions in walking.

As (a) in FIG. 4 shows, heel contact is a motion of the heel of the left foot (or the right foot) contacting the ground. When in this motion, the two legs are widely open, and thus the posture of the subject is low. More specifically, the waist (the head, chest, etc. as well) of the subject is in the lowest position.

As (b) in FIG. 4 shows, foot flat is a motion of the sole of the left foot (or the right foot) contacting the ground.

As (c) in FIG. 4 shows, mid stance is a motion of the two legs most closely approaching each other, with the sole of the left foot (or the right foot) contacting the ground. When in this motion, the left leg contacting the ground is stretched straight, and thus the posture of the subject is high. More specifically, the waist of the subject is in the highest position.

As (d) in FIG. 4 shows, heel off is a motion of the heel of the left foot (or the right foot) leaving the ground. When in this motion, the two legs are widely open, and thus the posture of the subject is low. More specifically, the waist of the subject is in the lowest position.

As (e) in FIG. 4 shows, toe off is a motion of the toe of the left foot (or the right foot) leaving the ground.

As (f) in FIG. 4 shows, mid swing is a motion of the two legs most closely approaching each other, with the left foot (or the right foot) leaving the ground. When in this motion, the right leg contacting the ground is stretched straight, and thus the posture of the subject is high. More specifically, the waist of the subject is in the highest position.

The same is true of the right foot. In the present embodiment, the motions of the left foot and the motions of the right foot have the following correspondences: as (a) in FIG. 4 shows, the heel contact of the left foot corresponds to the heel off of the right foot; as (b) in FIG. 4 shows, the foot flat of the left foot corresponds to the toe off of the right foot; as (c) in FIG. 4 shows, the mid stance of the left foot corresponds to the mid swing of the right foot; as (d) in FIG. 4 shows, the heel off of the left foot corresponds to the heel contact of the right foot; as (e) in FIG. 4 shows, the toe off of the left foot corresponds to the foot flat of the right foot; and as (f) in FIG. 4 shows, the mid swing of the left foot corresponds to the mid stance of the right foot.

Meanwhile, when the left leg is in stance phase, the center of gravity of the subject is located on the left foot, and thus the subject is in a left-leaning posture. More specifically, the waist of the subject leans to the left compared to when the subject is standing upright. Meanwhile, when the right leg is in stance phase, the center of gravity of the subject is located on the right foot, and thus the subject is in a right-leaning posture. More specifically, the waist of the subject leans to the right compared to when the subject is standing upright.

For example, when the left foot is in mid stance (the mid swing of the right foot) shown in (c) in FIG. 4, the greatest center of gravity is located on the left foot, and thus the waist of the subject is in the leftmost position. Similarly, when the right foot is in mid stance (the mid swing of the left foot) shown in (f) in FIG. 4, the greatest center of gravity is located on the right foot, and thus the waist of the subject is in the rightmost position. Meanwhile, when one of the feet is in heel contact (the heel off of the other foot) shown in (a) or (d) in FIG. 4, the subject is in the lowest and thus a stable posture, and the center of gravity is approximately the same as that of when the subject is standing upright.

Relationship Between Displacement Data and Motions of Subject

Next, a relationship between the horizontal displacement data/the vertical displacement data and the motions of subject 2 is described with reference to FIG. 5.

Figure 5:
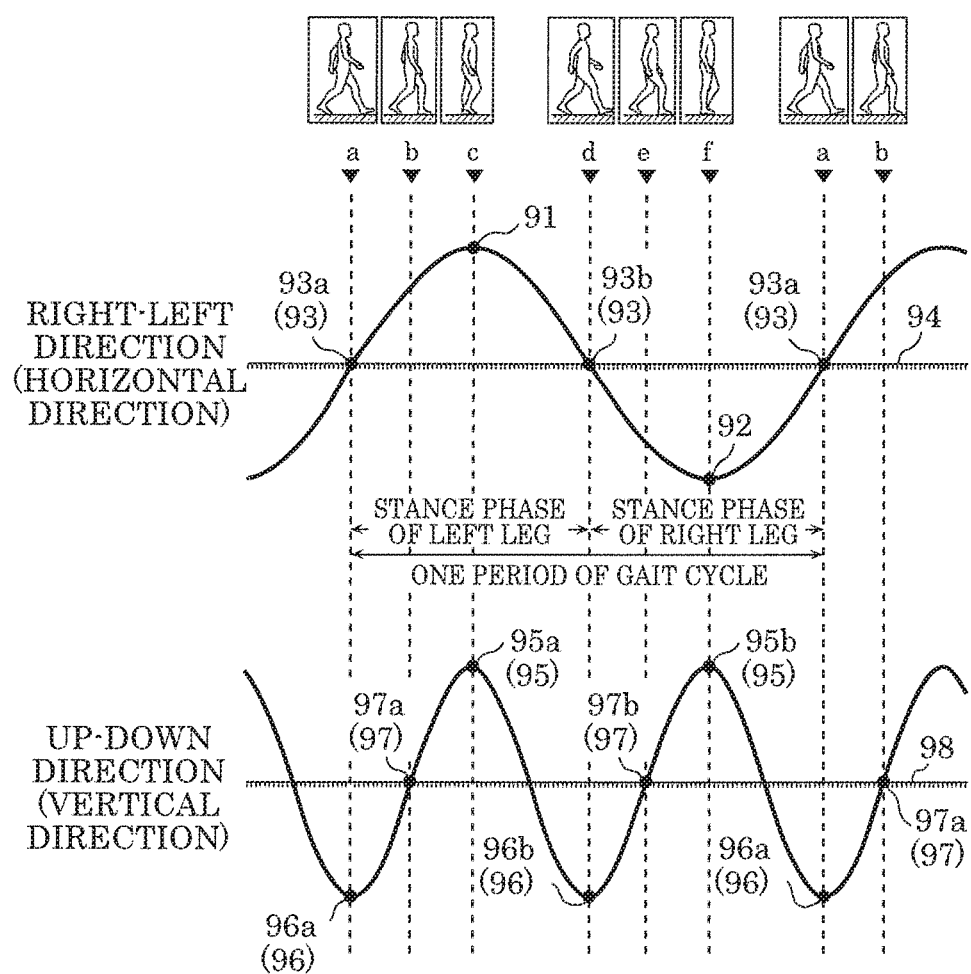
FIG. 5 is a diagram showing a relationship between horizontal and vertical displacement data and the representative motions of gait motions in the gait motion display system according to the embodiment.

FIG. 5 is a diagram showing a relationship between the horizontal and vertical displacement data and the representative motions of the gait motions in gait motion display system 1 according to the present embodiment. Note that the horizontal (right-left direction) displacement data and the vertical (up-down direction) displacement data shown in FIG. 5 are based on ideal gait motions. In FIG. 5, the lateral axis indicates the walking time, and the longitudinal axis indicates the amount of displacement in the horizontal direction or the vertical direction.

As shown in FIG. 5, the horizontal displacement data and the vertical displacement data are both in curves that are analogous to sinusoidal curves. As such, the horizontal displacement data and the vertical displacement data each include local maximum values and local minimum values that appear alternately and repeatedly. Zero-crossing points appear between a local maximum value and a local minimum value, and between a local minimum value and a local maximum value.

Horizontal (Right-Left Direction) Displacement Data

The horizontal displacement data is data that indicates displacements of a body part at which triaxial accelerometer 10 is attached (more specifically, the waist of subject 2), and that indicates displacements of subject 2 in the right-left direction. The horizontal displacement data represents, for example, a leftward displacement of subject 2 as being positive and a rightward displacement of subject 2 as being negative.

Local maximum value 91 in the horizontal displacement data is the point at which the maximum leftward displacement takes place in one period of the gait cycle. More specifically, local maximum value 91 corresponds to the motion in which the waist of subject 2 is in the leftmost position, i.e., the mid stance of the left foot (the mid swing of the right foot) shown in (c) in FIG. 4.

Local minimum value 92 in the horizontal displacement data is the point at which the maximum rightward displacement takes place in one period of the gait cycle. More specifically, local minimum value 92 corresponds to the motion in which the waist of subject 2 is in the rightmost position, i.e., the mid stance of the right foot (the mid swing of the left foot) shown in (f) in FIG. 4.

Zero-crossing points 93 in the horizontal displacement data indicate that no displacement of subject 2 takes place in the right-left direction. More specifically, zero-crossing points 93 correspond to the heel contact (or the heel off) of the left foot or the right foot of subject 2. Even more specifically, zero-crossing point 93a that appears between local minimum value 92 and local maximum value 91 corresponds to the heel contact of the left foot (the heel off of the right foot) shown in (a) in FIG. 4. Zero-crossing point 93b that appears between local maximum value 91 and local minimum value 92 corresponds to the heel contact of the right foot (the heel off of the left foot) shown in (d) in FIG. 4.

Here, a period from zero-crossing point 93a to the next zero-crossing point 93a is a single period of the gait cycle. A period from zero-crossing point 93a to zero-crossing point 93b is the stance phase of the left leg (i.e., a period during which the left foot is in contact with the ground). A period from zero-crossing point 93b to zero-crossing point 93a is the stance phase of the right leg (i.e., a period during which the right foot is in contact with the ground).

Note that zero-crossing points 93 are intersection points of the horizontal displacement data and zero baseline 94. Zero baseline 94 is determined, for example, as the mean value of a plurality of local maximum values 91 and a plurality of local minimum values 92.

Vertical (Up-Down Direction) Displacement Data

The vertical displacement data is data that indicates displacements of a body part at which triaxial accelerometer 10 is attached (more specifically, the waist of subject 2), and that indicates displacements of subject 2 in the up-down direction. The vertical displacement data represents, for example, an upward displacement of subject 2 as being positive and a downward displacement of subject 2 as being negative.

Local maximum values 95 in the vertical displacement data are points at which the maximum upward displacement takes place in one period of the gait cycle. More specifically, local maximum values 95 correspond to the motion in which the waist of subject 2 is in the highest position, i.e., mid stance (or mid swing).

Here, it is unknown only from the vertical displacement data whether local maximum values 95 correspond to the mid stance of the left foot or the mid stance of the right foot. As such, the horizontal displacement data is used to determine which one of the feet the mid stance belongs to. More specifically, local maximum value 95a is the local maximum value of the stance phase of the left leg, and thus corresponds to the mid stance of the left foot (the mid swing of the right foot) shown in (c) in FIG. 4. Also, local maximum value 95b is the local maximum value of the stance phase of the right leg, and thus corresponds to the mid stance of the right foot (the mid swing of the left foot) shown in (f) in FIG. 4.

Local minimum values 96 in the vertical displacement data are points at which the maximum downward displacement takes place in one period of the gait cycle. More specifically, local minimum values 96 correspond to the motion in which the waist of subject 2 is in the lowest position, i.e., heel contact (or heel off).

As in the case of local maximum values 95, the horizontal displacement data is used to determine whether local minimum values 96 correspond to the heel contact of the right foot or the left foot. More specifically, local minimum value 96a corresponds to the timing at which the stance phase of the left leg starts, and thus corresponds to the heel contact of the left foot (the heel off of the right foot) shown in (a) in FIG. 4. Also, local minimum value 96b corresponds to the timing at which the stance phase of the right leg starts, and thus corresponds to the heel contact of the right foot (the heel off of the left foot) shown in (d) in FIG. 4.

Zero-crossing points 97 in the vertical displacement data indicate that no displacement of subject 2 takes place in the up-down direction. More specifically, zero-crossing points 97 correspond to foot flat (or toe off) of subject 2.

As in the case of local maximum values 95 and local minimum values 96, the horizontal displacement data is used to determine whether zero-crossing points 97 correspond to the foot flat of the right foot or the left foot. More specifically, zero-crossing point 97a is the zero-crossing point in the stance phase of the left leg, and thus corresponds to the foot flat of the left foot (the toe off of the right foot) shown in (b) in FIG. 4. Also, zero-crossing point 97b is the zero-crossing point in the stance phase of the right leg, and thus corresponds to the foot flat of the right foot (the toe off of the left foot) shown in (e) in FIG. 4.

Note that zero-crossing points 97 are intersection points of the vertical displacement data and zero baseline 98. More specifically, zero-crossing points 97 are each zero-crossing point between local minimum value 96 and local maximum value 95. Zero baseline 98 is determined, for example, as the mean value of a plurality of local maximum values 95 and a plurality of local minimum values 96.

Reporting Screen

Figure 6:
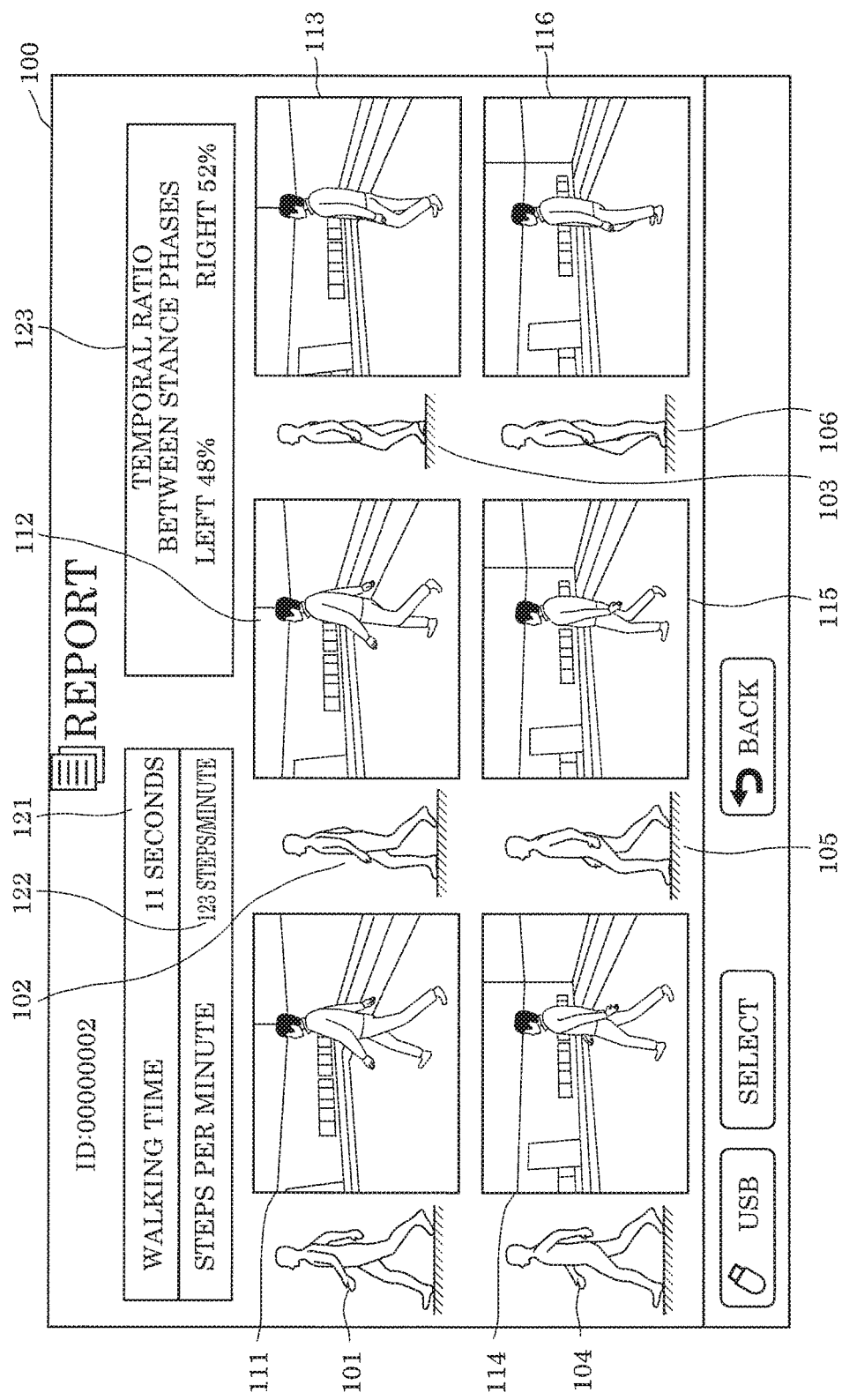
FIG. 6 is a diagram showing an example reporting screen displayed by a display of the gait motion display system according to the embodiment.

Next, a reporting screen displayed by display 34 will be described with reference to FIG. 6. FIG. 6 is a diagram showing an example of reporting screen 100 displayed by display 34 of gait motion display system 1 according to the present embodiment.

Reporting screen 100 is a screen displayed by display 34 to present the representative images identified by identification unit 33 to, for example, subject 2. Reporting screen 100 also includes information indicating the walking time, the number of steps per unit of time, and the right-left gait balance calculated by identification unit 33. More specifically, as shown in FIG. 6, reporting screen 100 includes a plurality of image illustrations 101 to 106, a plurality of representative images 111 to 116, walking time information 121, step information 122, and balance information 123.

In the present embodiment, a plurality of image illustrations 101 to 106 and a plurality of representative images 111 to 116 corresponding to the respective image illustrations 101 to 106 are placed side by side. More specifically, the image illustrations and their corresponding representative images are placed side by side in a lateral direction or in a vertical direction such that their correspondences can be seen at a glance. Note that the image illustrations and their representative images may be, for example, superimposed on each other to be displayed.

Image illustration 101 is an image illustration of the heel contact of the right foot shown in (d) in FIG. 4. Representative image 111, which is included in the moving image data, is an image corresponding to the time of the characteristic point corresponding to the heel contact of the right foot (more specifically, local minimum value 96b).

Image illustration 102 is an image illustration of the foot flat of the right foot shown in (e) in FIG. 4. Representative image 112, which is included in the moving image data, is an image corresponding to the time of the characteristic point corresponding to the foot flat of the right foot (more specifically, zero-crossing 97b).

Image illustration 103 is an image illustration of the mid stance of the right foot shown in (f) in FIG. 4. Representative image 113, which is included in the moving image data, is an image corresponding to the time of the characteristic point corresponding to the mid stance of the right foot (more specifically, local maximum value 95b).

Image illustration 104 is an image illustration of the heel contact of the left foot shown in (a) in FIG. 4. Representative image 114, which is included in the moving image data, is an image corresponding to the time of the characteristic point corresponding to the heel contact of the left foot (more specifically, local minimum value 96a).

Image illustration 105 is an image illustration of the foot flat of the left foot shown in (b) in FIG. 4. Representative image 115, which is included in the moving image data, is an image corresponding to the time of the characteristic point corresponding to the foot flat of the left foot (more specifically, zero-crossing 97a).

Image illustration 106 is an image illustration of the mid stance of the left foot shown in (c) in FIG. 4. Representative image 116, which is included in the moving image data, is an image corresponding to the time of the characteristic point corresponding to the mid stance of the left foot (more specifically, local maximum value 95a).

Walking time information 121 represents the walking time calculated by identification unit 33 in numerical values. Identification unit 33 calculates, as the walking time, a period of time during which the images of the gait motions of subject 2 have been taken properly and during which the acceleration has been detected. More specifically, identification unit 33 calculates, as the walking time, a period during which the acceleration data and the moving image data are recorded in synchronization with each other by recording unit 31.

Step information 122 indicates the number of steps per unit of time calculated by identification unit 33. A single step taken by subject 2 is represented as local maximum value 91 or local minimum value 92 in the horizontal displacement data. As such, identification unit 33 counts local maximum values 91 and local minimum values 92 in the walking time, and divides the counted total value (i.e., the number of steps) by the walking time to calculate the number of steps per unit of time.

Note that identification unit 33 may count the number of zero-crossing points 93 instead of calculating the total value of local maximum values 91 and local minimum values 92. Alternatively, identification unit 33 may count one of local maximum values 95, local minimum values 96, and zero-crossing points 97 in the vertical displacement data.

Balance information 123 indicates a ratio between the right and left stance phases calculated by identification unit 33. In the present embodiment, identification unit 33 extracts zero-crossing points 93 in the horizontal displacement data to calculate the durations of the right and left stance phases. The stance phase of the left leg is a period from zero-crossing point 93a to zero-crossing point 93b, and the stance phase of the right leg is a period from zero-crossing point 93b to zero-crossing point 93a. The walking time includes a plurality of stance phases of each of the left leg and the right leg, and thus identification unit 33 calculates the mean value or the intermediate value of the stance phases of the left leg and the mean value or the intermediate value of the stance phases of the right leg. For example, identification unit 33 calculates a ratio between the mean value of the stance phases of the left leg and the mean value of the stance phases of the right leg as a proportion between the right and left stance phases.

Detailed Operations of Identification Unit

The following describes detailed operations of identification unit 33. More specifically, a method will be described below by which identification unit 33 identifies representative images 111 to 116 that correspond to image illustrations 101 to 106.

In the present embodiment, identification unit 33 first identifies the stance phases of the left leg and the stance phases of the right leg on the basis of the horizontal displacement data. Identification unit 33 further extracts, as characteristic points, local maximum values 95, local minimum values 96, and zero-crossing points 97 from the vertical displacement data to identify, as the representative images, the images corresponding to the times of the extracted characteristic points.

For example, identification unit 33 extracts local minimum values 96 in the vertical displacement data as characteristic points corresponding to heel contact. In so doing, in the case where local minimum value 96 is local minimum value 96a included in the stance phase of the left leg, identification unit 33 identifies the image corresponding to the time of local minimum value 96a as representative image 114. Consequently, image illustration 104 of the heel contact of the left foot and representative image 114 are displayed together on display 34. In the case where local minimum value 96 is local minimum value 96b included in the stance phase of the right leg, identification unit 33 identifies the image corresponding to the time of local minimum value 96b as representative image 111. Consequently, image illustration 101 of the heel contact of the right foot and representative image 111 are displayed together on display 34.

Note that identification unit 33 may extract zero-crossing points 93 in the horizontal displacement data as characteristic points corresponding to heel contact. More specifically, identification unit 33 may extract zero-crossing point 93a in the horizontal displacement data as the characteristic point corresponding to the heel contact of the left foot, and may extract zero-crossing point 93b in the horizontal displacement data as the characteristic point corresponding to the heel contact of the right foot.

Identification unit 33 also extracts zero-crossing points 97 in the vertical displacement data as characteristic points corresponding to foot flat. In so doing, in the case where zero-crossing point 97 is zero-crossing point 97a included in the stance phase of the left leg, identification unit 33 identifies the image corresponding to the time of zero-crossing point 97a as representative image 115. Consequently, image illustration 105 of the foot flat of the left foot and representative image 115 are displayed together on display 34. In the case where zero-crossing point 97 is zero-crossing point 97b included in the stance phase of the right leg, identification unit 33 identifies the image corresponding to the time of zero-crossing point 97b as representative image 112. Consequently, image illustration 102 of the foot flat of the right foot and representative image 112 are displayed together on display 34.

Note that identification unit 33 may identify representative image 112 or 115 on the basis of the horizontal displacement data. More specifically, identification unit 33 may identify, as representative image 112, the image corresponding to the time in between local minimum value 92 and zero-crossing point 93b (e.g., the time corresponding to the midpoint between these two points) in the horizontal displacement data. Also, identification unit 33 may identify, as representative image 115, the image corresponding to the time in between zero-crossing point 93a and local maximum value 91 (e.g., the time corresponding to the midpoint between these two points) in the horizontal displacement data.

Identification unit 33 also extracts local maximum values 95 in the vertical displacement data as characteristic points corresponding to mid stance. In so doing, in the case where local maximum value 95 is local maximum value 95a included in the stance phase of the left leg, identification unit 33 identifies the image corresponding to the time of local maximum value 95a as representative image 116. Consequently, image illustration 106 of the mid stance of the left foot and representative image 116 are displayed together on display 34. In the case where local maximum value 95 is local maximum value 95b included in the stance phase of the right leg, identification unit 33 identifies the image corresponding to the time of local maximum value 95b as representative image 113. Consequently, image illustration 105 of the mid stance of the right foot and representative image 115 are displayed together on display 34.

Embodiment

Figure 7:
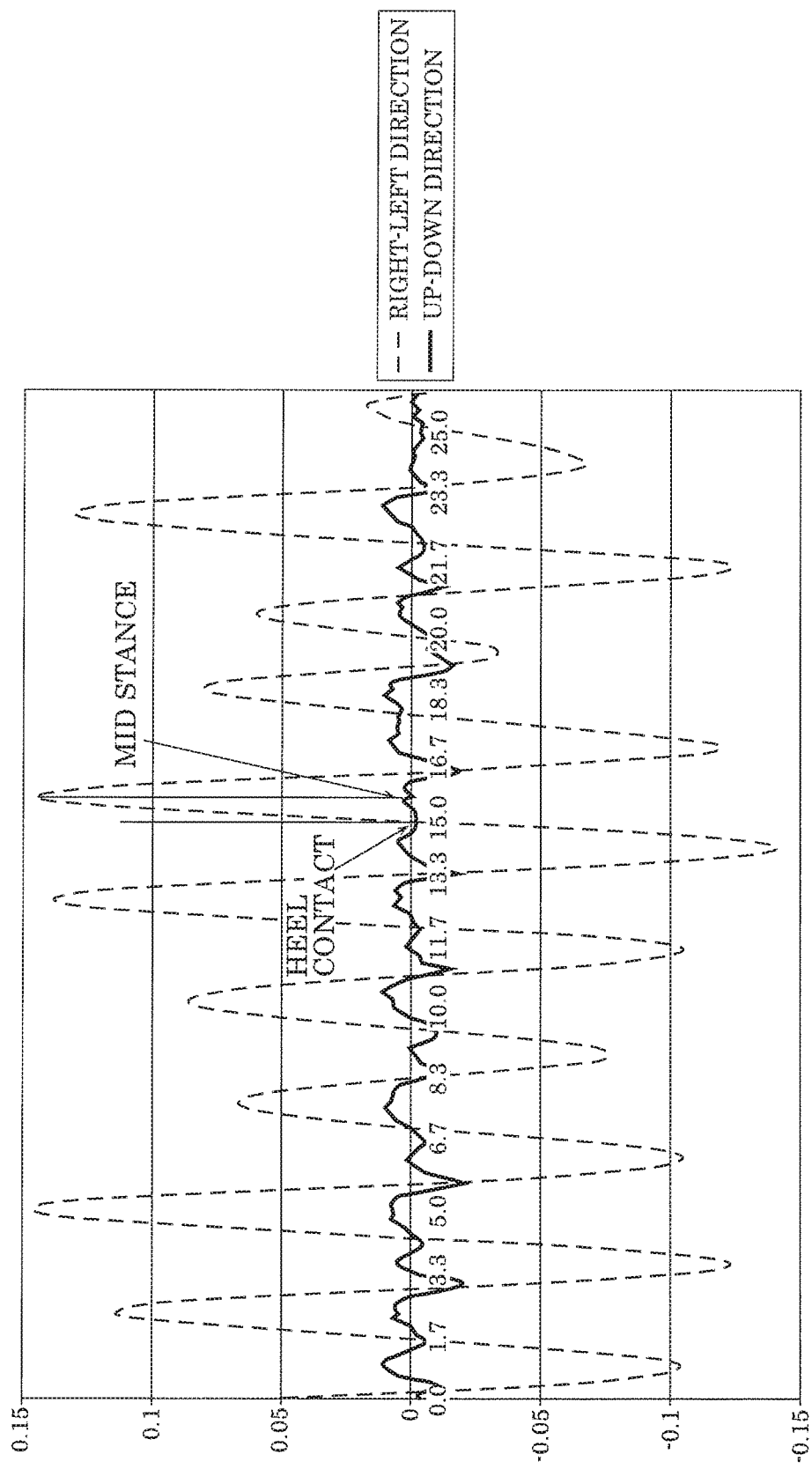
FIG. 7 is a diagram showing horizontal and vertical displacement data converted from acceleration data that has been actually measured by the triaxial accelerometer in the gait motion display system according to the embodiment.
Figure 8:
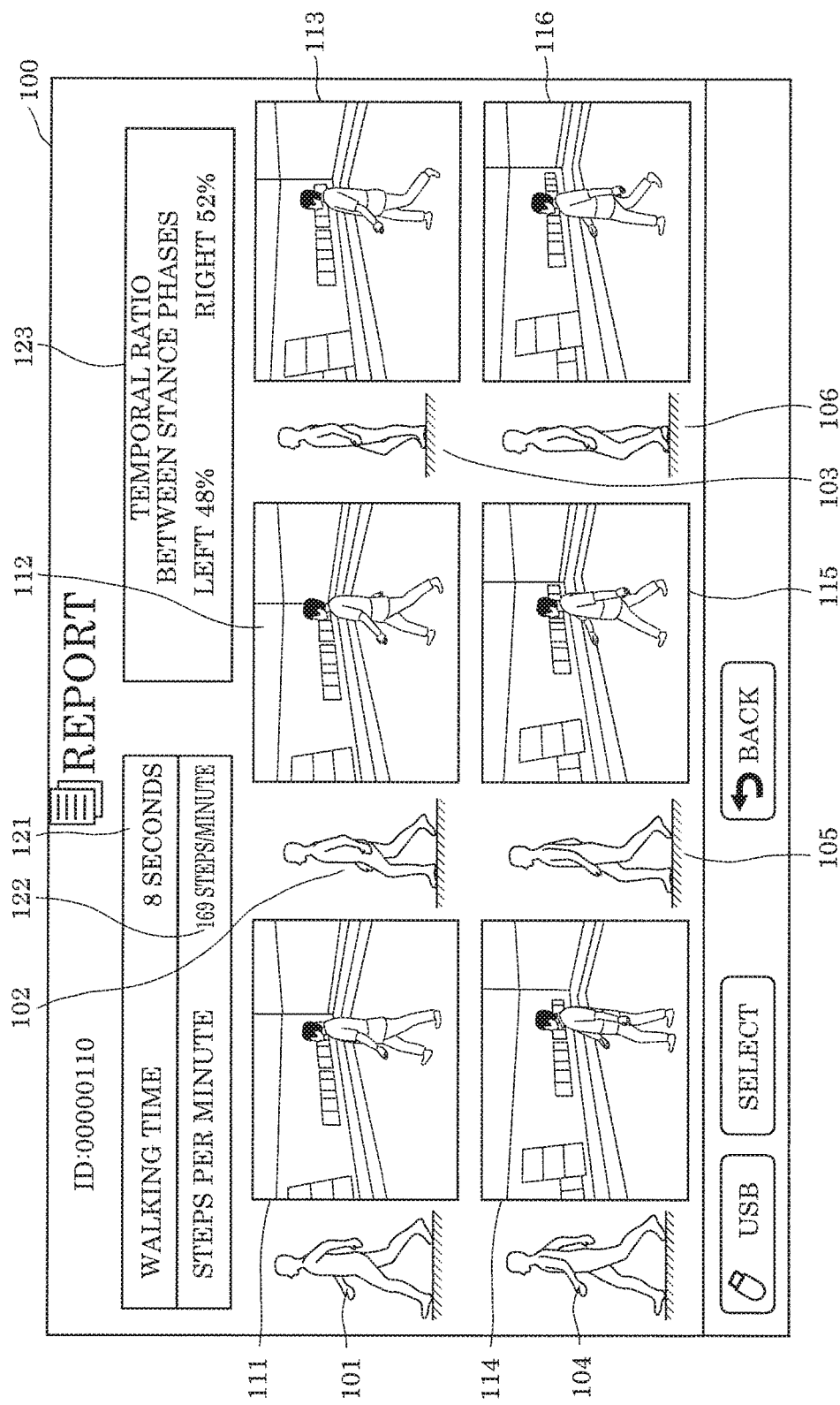
FIG. 8 is a diagram showing another example of the reporting screen displayed by the display of the gait motion display system according to the embodiment.

With reference to FIG. 7 and FIG. 8, the following describes an embodiment in which measurements and taking of images are performed, with triaxial accelerometer 10 being attached to a real person as subject 2. Note that the embodiment employs as subject 2 a person who has difficulty in walking properly. For this reason, the report screen displayed by display 34 shows discrepancies between the motions represented by image illustrations and the motions represented by representative images.

FIG. 7 is a diagram showing horizontal displacement data and vertical displacement data converted from acceleration data that has been actually measured by triaxial accelerometer 10 in gait motion display system 1 according to the present embodiment. Note that the lateral axis indicates the walking time, and the vertical axis indicates the amount of displacement in the horizontal direction and the vertical direction.

As shown in FIG. 7, it is deemed difficult to extract local maximum values and local minimum values from the actual displacement data. When the gait motions of subject 2 are improper, the movements of the center of gravity mismatch the gait motions. As a result, there might be a significant difference in the gait cycles between the horizontal displacement data and the vertical displacement data For example, the horizontal displacement data shown in FIG. 7 indicates that a single period of the gait cycle is about 3.3 seconds to 3.4 seconds. Meanwhile, it is difficult, with the vertical displacement data shown in FIG. 7, to identify the gait cycle because of such a factor as uncertainty of the timing at which the local maximum values and local minimum values appear. For example, a single period of 13.3 seconds to 16.7 seconds includes three local maximum values and three local minimum values in the vertical displacement data.

In such a case as this where the extraction of characteristic points from the vertical displacement data is difficult, identification unit 33 is capable of extracting characteristic points from the horizontal displacement data without using the vertical displacement data. For example, when the dispersion in one period of the gait cycle in the vertical displacement data is greater than a predetermined value, identification unit 33 extracts characteristic points from the horizontal displacement data, judging that the extraction of characteristic points from the vertical displacement data is difficult.

For example, identification unit 33 extracts, as the characteristic point corresponding to the heel contact of the left foot, a zero-crossing point (e.g., the zero-crossing point at the time point of about 15.0 seconds) from the horizontal displacement data. Identification unit 33 identifies the image corresponding to the time of the extracted zero-crossing point (15.0 seconds) as representative image 114 to be displayed together with image illustration 104 of the heel contact of the left foot.

Similarly, identification unit 33 extracts, as the characteristic point corresponding to the mid stance of the left foot, a local maximum value (e.g., the local maximum value at the time point of about 15.8 seconds) from the horizontal displacement data. Identification unit 33 identifies the image corresponding to the time of the extracted local maximum value (15.8 seconds) as representative image 116 to be displayed together with image illustration 106 of the mid stance of the left foot.

FIG. 8 is a diagram showing an example of reporting screen 100 displayed by display 34 of gait motion display system 1 according to the present embodiment.

As shown in FIG. 7, the movements of the center of gravity mismatch the gait motions of subject 2 in the case where such gait motions are improper. As such, when representative images are identified on the basis of the horizontal displacement data or the vertical displacement data, the motions represented by the image illustrations mismatch the motions represented by the representative images.

For example, in reporting screen 100 shown in FIG. 8, the motions represented by representative images 111 to 116 mismatch the motions represented by image illustrations 101 to 106. For this reason, by visually checking reporting screen 100, subject 2 or an instructor can judge whether the gait motions are properly made, or can see the extent of the discrepancies in the case where such gait motions are improper. As described above, gait motion display system 1 according to the present embodiment is capable of assisting the coaching for proper gait motions with a simple structure.

Effects, Etc.

As described above, gait motion display system 1 according to the present embedment includes: triaxial accelerometer 10 that measures acceleration data of subject 2 in walking, triaxial accelerometer 10 being attached to subject 2; imaging unit 20 that takes images of subject 2 in walking to obtain moving image data showing gait motions of subject 2; recording unit 31 that records the acceleration data and the moving image data in synchronization with each other; identification unit 33 that converts the acceleration data recorded by recording unit 31 into horizontal displacement data and vertical displacement data, and identifies, from the moving image data, a representative image corresponding to a representative motion in a gait cycle, based on the horizontal displacement data or the vertical displacement data; and display 34 that displays an image illustration of the representative motion in the gait cycle, together with the representative image identified by identification unit 33.

This provides a highly convenient gait motion display system 1 with a simple structure that includes triaxial accelerometer 10 and imaging unit 20 (video camera). More specifically, this structure enables a representative image to be identified on the basis of the horizontal displacement data or the vertical displacement data converted from the acceleration data measured by triaxial accelerometer 10 and to be displayed together with its image illustration. Consequently, the gait motions can be checked with ease even in the absence, for example, of a skilled observer.

Moreover, identification unit 33, for example, extracts a characteristic point from the horizontal displacement data or the vertical displacement data, and identifies an image corresponding to a time of the extracted characteristic point as the representative image, the characteristic point corresponding to the representative motion in the gait cycle.

For example, a body part of subject 2 at which triaxial accelerometer 10 is attached undergoes periodic displacements in accordance with the gait motions of subject 2. As such, the horizontal displacement data or the vertical displacement data converted from the acceleration data measured by triaxial accelerometer 10 periodically changes in accordance with the representative motions in the gait cycle. The characteristic points included in the displacement data correspond to the representative motions in the gait cycle, and thus the extraction of the characteristic points from the displacement data enables easy and precise identification of representative images. Consequently, by checking correspondences between image illustrations and their representative images, it is possible to easily judge whether the gait motions are properly made by subject 2, and thus to assist the coaching for gait motions Also, the characteristic point is, for example, one of a local maximum value, a local minimum value, and a zero-crossing point in the horizontal displacement data or the vertical displacement data.

This structure uses a local maximum value, a local minimum value, or a zero-crossing point as a characteristic point, and thus allows for easy extraction of the characteristic point.

Also, the representative motion in the gait cycle is, for example, at least one of heel contact, foot flat, mid stance, heel off, and toe off, which are selected from a stance phase and a swing phase.

This enables display 34 to display a characteristic motion of the gait motions such as heel contact, and thus makes it easier to provide coaching for gait motions of subject 2. For example, when the motion represented by an image illustration is approximately the same as the motion represented by its representative image to be displayed together with such image illustration, it is possible to see that the gait motion is properly made. When the motion represented by an image illustration differs from the motion represented by its representative image to be displayed together with such image illustration, it is possible to present to subject 2 the extent of the discrepancy from the proper gait motion, and thus to assist the coaching for proper gait motions.

Identification unit 33 further calculates, for example, walking time and the number of steps per predetermined unit of time, based on the horizontal displacement data or the vertical displacement data, and display 34 further displays the walking time and the number of steps calculated by identification unit 33.

This allows display 34 to display the walking time and the number of steps per unit of time, thereby assisting the coaching concerning, for example, the gait speed in the gait motions of subject 2.

Identification unit 33 further calculates, for example, a ratio between right and left stance phases, based on the horizontal displacement data or the vertical displacement data, and display 34 further displays the ratio calculated by identification unit 33.

This allows display 34 to display the ratio between the right and left stance phases, thereby assisting the coaching for improving the right and left balance in the gait motions of subject 2.

Note that the technology of the present embodiment can be embodied not only as a gait motion display system, but also as a program that causes a computer to function as the above-described gait motion display system. Alternatively, the technology of the present embodiment can be embodied as a computer-readable recording medium such as a digital versatile disc (DVD) storing such program.

Stated differently, the above-described comprehensive or specific embodiment can be achieved in the form of a system, a device, an integrated circuit, a computer program, or a computer-readable recording medium, or can be achieved in the form of a combination of any of a system, a device, an integrated circuit, a computer program, and a recording medium.

Others

The gait motion display system according to the present invention has been described on the basis of the embodiment and its variations, but the present invention is not limited to such embodiment.

For example, the foregoing embodiment presents an example in which identification unit 33 identifies representative images on the basis of both the horizontal displacement data and the vertical displacement data, but the present invention is not limited to this. Identification unit 33 may identify representative images on the basis of only the horizontal displacement data or the vertical displacement data.

Also, the foregoing embodiment presents an example in which identification unit 33 calculates the walking time, the number of steps per unit of time, and the temporal ratio between the stance phases, and display 34 displays these items of information, but the present invention is not limited to this. For example, display 34 may not display at least one of walking time information 121, step information 122, and balance information 123 shown in FIG. 6. Also, balance information 123 indicates the temporal ratio between the right and left stance phases, but balance information 123 may indicate the temporal ratio between the right and left swing phases.

Also, the foregoing embodiment presents an example in which display 34 takes the form of a computer monitor as shown in FIG. 1, but the present invention is not limited to this. Display 34 may be, for example, a monitor of a video camera (imaging unit 20)

Moreover, in the above embodiment, each structural component may be materialized as dedicated hardware, or may be achieved by executing a software program suited to each structural component. Alternatively, each structural component may be achieved by reading and executing, by a program execution unit such as a central processing unit (CPU) or a processor, a software program recorded in a recording medium such as a hard disk or a semiconductor memory.

The present invention also includes embodiments achieved by making various modifications to the present embodiment that are conceivable by those skilled in the art, and embodiments achieved by combining any structural components and functions of the present embodiment without materially departing from the essence of the present invention.

The invention claimed is:

1. A gait motion display system comprising:
a triaxial accelerometer configured to measure acceleration data of a subject in walking, the triaxial accelerometer configured to be attached to the subject;
a camera configured to take images of the subject in walking to obtain moving image data showing gait motions of the subject;
memory configured to record the acceleration data from the triaxial accelerometer and the moving image data in synchronization with each other, wherein:
the acceleration data includes a plurality of measurement points associated with time information; and
the moving image data includes a plurality of images associated with time information;
a processor configured to:
convert the acceleration data recorded by the memory from the triaxial accelerometer into horizontal displacement data and vertical displacement data,
extract a characteristic point from the horizontal displacement data or the vertical displacement data, the characteristic point corresponding to a representative motion in an ideal gait cycle,
after the extraction of the characteristic point, identify the time information associated with the extracted characteristic point, and
after the identification of the time information associated with the extracted characteristic point, identify, from the plurality of images, an image recorded in the memory that corresponds with the time information associated with the identified time information of the extracted characteristic point, as a representative image of the gait motion of the subject, using the identified time information; and
a display configured to display an image illustration of the representative motion in the ideal gait cycle and the representative image identified by the processor separately side by side to enable simultaneous visual comparison of the representative motion in the ideal gait cycle and a corresponding gait motion of the subject.

2. The gait motion display system according to claim 1, wherein the characteristic point is one of a local maximum value, a local minimum value, and a zero-crossing point in the horizontal displacement data or the vertical displacement data.

3. The gait motion display system according to claim 1, wherein the representative motion in the gait cycle is at least one of heel contact, foot flat, mid stance, heel off, and toe off, which are selected from a stance phase and a swing phase.

4. The gait motion display system according to claim 1, wherein the processor further calculates walking time and a number of steps per predetermined unit of time, based on the horizontal displacement data or the vertical displacement data, and
the display further displays the calculated walking time and the calculated number of steps.

5. The gait motion display system according to claim 1, wherein the processor further calculates a ratio between right and left stance phases, based on the horizontal displacement data or the vertical displacement data, and
the display further displays the ratio calculated by the processor.

6. A non-transitory computer-readable recording medium storing a program that causes a computer to execute a gait motion display method comprising:
obtaining, from a triaxial accelerometer configured to be attached to a subject, acceleration data of the subject in walking;
obtaining, from a camera configured to take images of the subject in walking, moving image data showing gait motions of the subject;
recording, into a memory, the acceleration data from the triaxial accelerometer and the moving image data in synchronization with each other, wherein:
the acceleration data includes a plurality of measurement points associated with time information; and
the moving image data includes a plurality of images associated with time information;
converting the acceleration data recorded in the memory from the triaxial accelerometer into horizontal displacement data and vertical displacement data;
extracting a characteristic point from the horizontal displacement data or the vertical displacement data, the characteristic point corresponding to a representative motion in an ideal gait cycle;
after the extraction of the characteristic point, identifying the time information associated with the extracted characteristic point, and
after the identifying of the time information associated with the extracted characteristic point, identifying, from the plurality of images, an image recorded in the memory that corresponds with the time information associated with the identified time information of the extracted characteristic point, as a representative image of the gait motion of the subject, using the identified time information; and
displaying an image illustration of the representative motion in the ideal gait cycle and the representative image identified in the identifying separately side by side to enable simultaneous visual comparison of the representative motion in the ideal gait cycle and a corresponding gait motion of the subject.

* * * * *